United States Patent
Shimauchi et al.

(10) Patent No.: US 11,096,618 B2
(45) Date of Patent: Aug. 24, 2021

(54) SIGNAL FEATURE EXTRACTION APPARATUS, SIGNAL FEATURE EXTRACTION METHOD, AND PROGRAM

(71) Applicant: NIPPON TELEGRAPH AND TELEPHONE CORPORATION, Chiyoda-ku (JP)

(72) Inventors: Suehiro Shimauchi, Musashino (JP); Kana Eguchi, Yokosuka (JP); Tsutomu Yabuuchi, Yokosuka (JP); Kazuhiro Yoshida, Yokosuka (JP); Osamu Mizuno, Musashino (JP)

(73) Assignee: NIPPON TELEGRAPH AND TELEPHONE CORPORATION, Chiyoda-ku (JP)

( * ) Notice: Subject to any disclaimer, the term of this patent is extended or adjusted under 35 U.S.C. 154(b) by 68 days.

(21) Appl. No.: 16/465,251

(22) PCT Filed: Dec. 5, 2017

(86) PCT No.: PCT/JP2017/043661
§ 371 (c)(1),
(2) Date: May 30, 2019

(87) PCT Pub. No.: WO2018/105616
PCT Pub. Date: Jun. 14, 2018

(65) Prior Publication Data
US 2019/0290156 A1 Sep. 26, 2019

(30) Foreign Application Priority Data
Dec. 6, 2016 (JP) .............................. JP2016-236592

(51) Int. Cl.
*A61B 5/352* (2021.01)
*A61B 5/00* (2006.01)
(Continued)

(52) U.S. Cl.
CPC .............. *A61B 5/352* (2021.01); *A61B 5/024* (2013.01); *A61B 5/0816* (2013.01); *A61B 5/72* (2013.01)

(58) Field of Classification Search
CPC ....... G10L 25/90; G10L 25/18; A61B 5/0456; A61B 5/024; A61B 5/0816; A61B 5/726;
(Continued)

(56) References Cited

U.S. PATENT DOCUMENTS

| 2015/0126878 A1* | 5/2015 | An | A61B 5/7282 |
| | | | 600/484 |
| 2016/0120430 A1* | 5/2016 | Bayasi | A61B 5/0456 |
| | | | 600/516 |

(Continued)

OTHER PUBLICATIONS

International Search Report dated Feb. 20, 2018 in PCT/JP2017/043661 filed on Dec. 5, 2017.
(Continued)

*Primary Examiner* — Catherine M Voorhees
(74) *Attorney, Agent, or Firm* — Oblon, McClelland, Maier & Neustadt, L.L.P.

(57) ABSTRACT

The purpose of the present invention is to accurately identify an appearance position of a desired waveform pattern. A signal feature extraction apparatus extracts a feature peak value of a waveform pattern from an output signal of a feature extraction filter that extracts a waveform pattern of an input signal. A local maximum value detection part 1 stores a time index and a value of the output signal when an absolute value of the output signal is equal to or more than a predetermined threshold value and takes a local maximum value. A feature peak value selection part 2 selects a feature peak value on the basis of a difference between a time interval between the stored time index and a time index of a feature peak value selected immediately before and an average time interval at which the feature peak value can
(Continued)

occur, and a difference between a logarithmic amplitude and phase of the output signal corresponding to the stored time index and an average logarithmic amplitude and average phase that the feature peak value can take.

11 Claims, 2 Drawing Sheets

(51) Int. Cl.
 *A61B 5/024* (2006.01)
 *A61B 5/08* (2006.01)
(58) Field of Classification Search
 CPC ..... A61B 5/0205; A61B 5/1102; A61B 5/725; A61B 5/352; A61B 5/7203
 See application file for complete search history.

(56) References Cited

U.S. PATENT DOCUMENTS

| | | | |
|---|---|---|---|
| 2017/0156606 A1* | 6/2017 | Ferber | A61B 5/14539 |
| 2017/0311901 A1* | 11/2017 | Zhao | A61B 5/1102 |
| 2018/0160966 A1* | 6/2018 | Inan | A61B 7/006 |
| 2018/0235487 A1* | 8/2018 | Paul | A61B 5/7278 |
| 2019/0150794 A1* | 5/2019 | Vrudhula | G06N 3/0454 |

OTHER PUBLICATIONS

Vetterli, M. et al., "Wavelets and Filter Banks: Theory and Design," IEEE Transactions on Signal Processing, vol. 40, No. 9, Sep. 1992, pp. 2207-2232.

* cited by examiner

SIGNAL FEATURE EXTRACTION APPARATUS, SIGNAL FEATURE EXTRACTION METHOD, AND PROGRAM

TECHNICAL FIELD

The present invention relates to a technique for extracting features of a signal waveform of an acoustic signal, a biological signal, or the like.

BACKGROUND ART

As a feature extraction technique for analyzing features of an acoustic signal or a biological signal, there is analysis by a filter bank composed of a group of band-pass filters having different center frequencies and band widths (for example, see non-patent literature 1). For example, regarding a signal in which a similar waveform pattern (hereinafter also referred to as a feature) is continuously repeated, an output signal of a band-pass filter (hereinafter also referred to as a feature extraction filter) having an impulse response highly correlated with the waveform pattern takes a peak value (hereinafter also referred to as a feature peak value) in synchronization with an appearance of a target waveform pattern. For example, in analyzing intervals between heartbeats (RRI: R-R Interval), which is regarded as one of basic feature quantities in the analysis of biological information from an electrocardiogram waveform, it is important to accurately capture the feature peak value and identify time intervals of peak positions.

PRIOR ART LITERATURE

Non-Patent Literature

Non-patent literature 1: M. Vetterli and C. Herley, "Wavelets and filter banks: theory and design," in IEEE Transactions on Signal Processing, vol. 40, no. 9, pp. 2207-2232, September 1992.

SUMMARY OF THE INVENTION

Problems to be Solved by the Invention

However, in the prior art, the output of the feature extraction filter may show peaks other than a desired feature peak due to factors such as noise being mixed in with a signal to be analyzed. This may result in an erroneous peak position causing inappropriate RRI for feature analysis.

An object of the present invention is to provide a signal feature extraction technique that can accurately identify an appearance position of a desired waveform pattern output from a feature extraction filter with respect to a signal to be analyzed without being influenced by noise or the like and output it as a signal feature.

Means to Solve the Problems

In order to solve the above-described problem, a signal feature extraction apparatus of a first aspect of the present invention is a signal feature extraction apparatus that extracts a feature peak value of a waveform pattern from an output signal of a feature extraction filter that extracts a waveform pattern of an input signal, comprising a local maximum value detection part that stores a time index and a value of the output signal when an absolute value of the output signal is equal to or more than a predetermined threshold value and takes a local maximum value; and a feature peak value selection part that selects a feature peak value on the basis of a difference between a time interval between the stored time index and a time index of a feature peak value selected immediately before and an average time interval at which the feature peak value can occur, and a difference between a logarithmic amplitude and phase of the output signal corresponding to the stored time index and an average logarithmic amplitude and average phase that the feature peak value can take.

In order to solve the above-described problem, a signal feature extraction apparatus of a second aspect of the present invention is a signal feature extraction apparatus that extracts a feature peak value of a waveform pattern from an output signal of a feature extraction filter that extracts a waveform pattern of an input signal, comprising a local maximum value detection part that stores a time index and a value of the output signal when an absolute value of the output signal is equal to or more than a predetermined threshold value and takes a local maximum value; and a feature peak value selection part that selects a feature peak value on the basis of a difference between a time interval between the stored time index and a time index of a feature peak value selected immediately before and an average time interval at which the feature peak value can occur, a difference between an amplitude of the output signal corresponding to the stored time index and an average amplitude the feature peak value can take, and a difference between a phase of the output signal corresponding to the stored time index and an average phase the feature peak value can take.

Effects of the Invention

According to the invention, it is possible to accurately identify an appearance position of a desired waveform pattern output from a feature extraction filter for a signal to be analyzed without being influenced by noise or the like and output it as a signal feature.

DETAILED DESCRIPTION OF THE EMBODIMENTS

Figure 1:
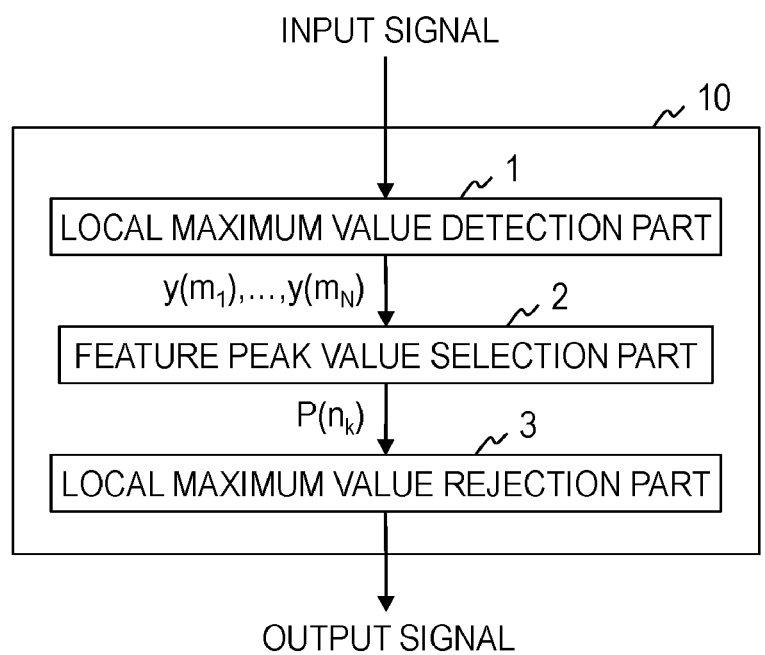
FIG. 1 is a diagram exemplifying a functional configuration of a signal feature extraction apparatus.

Symbols "~", "^", "-" and the like used herein should be written directly above an immediately following character, but due to restriction of text notation, they are written immediately before the character. In formulas, the symbols are written at their original position, that is, directly above the character.

In the following, consideration is given to processing about an output signal obtained when a certain signal is input into an analysis system including at least one or more feature extraction filters (for example, band-pass filters, wavelets, or other filters with nonlinear nature). However, the feature extraction filters are limited to linear or nonlinear filters that output as an output signal a complex signal having a real part and an imaginary part mutually convertible (or approximately convertible) by Hilbert transform.

The present invention is a signal feature extraction technique for selecting a peak value desired to be originally extracted as a feature peak value from peak values of an absolute value |y(n)| of an output signal y(n) output by a feature extraction filter with respect to an input signal to be analyzed. A signal feature extraction method according to the invention will be described below.

(1) It is assumed that a feature peak value of magnitude $P(n_0)$ is detected at time $n_0$ as an initial value. If there is no information beforehand, the initial value may be given a first observed peak value of the absolute value |y(n)| of the output signal y(n).

(2) Next, assuming that a time index when the absolute value |y(n)| of the complex output signal y(n) of the feature extraction filter is equal to or more than a predetermined threshold value and takes a local maximum value is denoted by $m_\lambda = n$, the value of the output signal y(n) is stored together with the time index $m_\lambda$. Here, the subscript $\lambda$, is an index of the time index of the stored local maximum value. The value of $\lambda$ is given as $\lambda=1$ if there is no local maximum value stored so far and $\lambda=N$ if there are N−1 local maximum values stored already.

(3) When a timer that measures a time when the local maximum value detection processing of (2) is being performed indicates that a certain time (for example, when an appearance interval of the feature peak value is $\Delta T$, $2\Delta T$ or the like corresponding to twice the appearance interval can be given) has passed, the timer is reset and it is confirmed whether a local maximum value has been detected. At this time, if no local maximum value is detected, a time index of a past feature peak value $P(n_{k-1})$ is updated and a new feature peak value $P(n_k)$ is allocated to a position of $n_k \leftarrow n_{k-1} + \Delta T$, because loss of the signal is suspected. Here, k is an index of an output feature peak value. The value of $P(n_k)$ can be selected from explicitly indicating that a peak is not detected by giving 0, and interpolating by giving the past feature peak value $P(n_{k-1})$ or its average value A.

(4) After the elapse of the certain time, if one or more local maximum values $y(m_\lambda)$ of the output signal have been detected, the feature peak value $P(n_k)$ is calculated by formulas (1) and (2) with respect to the stored local maximum values $y(m_1), y(m_2), \ldots, y(m_N)$ of the output signal.

$$n_k = \underset{m_\lambda}{\operatorname{argmin}} \left[ w_1 \frac{|m_\lambda - n_0 - \Delta T|^2}{\Delta T^2} + \frac{w_2 |\log(|y(m_\lambda)|) - \log\_A|^2 + w_3 |\mathrm{angle}(y(m_\lambda)/e^{j\Phi})|^2}{w_4 \log\_A^2 + w_5 \Phi^2} \right] \quad (1)$$

$$P(n_k) = |y(n_k)| \quad (2)$$

Here, log_A denotes an average logarithmic amplitude of the feature peak value (average of logarithmic amplitude or logarithm of average amplitude). The symbol $\Phi$ denotes an average phase value of the feature peak value. The symbol angle (x) denotes a function representing a phase angle of a complex number x. In the formula (1), weighting factors $w_1$, $w_2$, $w_3$, $w_4$, and $w_5$ are positive numbers to adjust which of the time difference, amplitude difference, and phase difference from an immediately before feature peak value should be emphasized in selecting the feature peak value from among the detected local maximum values.

(5) When the new feature peak value $P(n_k)$ is selected, only a local maximum value corresponding to a time index which is $n_k < m_\lambda$ among the stored local maximum values $y(m_1), y(m_2), \ldots, y(m_N)$ is left and the rest are rejected. In addition, the index of the feature peak value is updated to $k \leftarrow k+1$ and the processing returns to that of (2).

The average time interval $\Delta T$ when the feature peak value appears, average logarithmic amplitude log_A, and average phase $\Phi$ may be given fixed values or may be sequentially updated on the basis of information on the feature peak value $P(n_k)$ detected newly by the processing of (4) (and past information). If it is updated whenever a new feature peak value $P(n_k)$ is selected, for example, it can be updated by a formula (3).

$$\Delta T \leftarrow \mu_1 \Delta T + (1 - \mu_1)(n_k - n_{k-1}) \quad (3)$$
$$\log\_A \leftarrow \mu_2 \log\_A + (1 - \mu_2) \log(|y(n_k)|)$$
$$\Phi \leftarrow \mathrm{angle}\left( (e^{j\Phi})^{\mu_3} \left( \frac{y(n_k)}{|y(n_k)|} \right)^{1-\mu_3} \right)$$

Here, μ1, μ2, and μ3 are adjustment coefficients for taking a value in the range of 0 to 1 and adjusting a weighted average with past estimated values. The validity of the detected feature peak value $P(n_k)$ can be evaluated by the magnitude of an error E calculated by a formula (4).

$$E = \underset{m_\lambda}{\min} \left[ w_1 \frac{|m_\lambda - n_0 - \Delta T|^2}{\Delta T^2} + \frac{w_2 |\log(|y(m_\lambda)|) - \log\_A|^2 + w_3 |\mathrm{angle}(y(m_\lambda)/e^{j\Phi})|^2}{w_4 \log\_A^2 + w_5 \Phi^2} \right] \quad (4)$$

Depending on a difference in the magnitude of the error E, values of the weighting factors $w_1$, $w_2$, $w_3$, $w_4$, and $w_5$ in the formula (1) and the adjustment coefficients $\mu_1$, $\mu_2$, and $\mu_3$ in the formula (3) may be switched and given. Control can be performed, for example, when the magnitude of the error E is smaller, the values of the adjustment coefficients $\mu_1$, $\mu_2$, and $\mu_3$ can be given smaller values and the degree of reflection of latest information can be increased.

An embodiment of the invention will be described below in detail. Constituent parts having the same functions in the drawings are given the same identification numbers and redundant explanation will be omitted.

A signal feature extraction apparatus 10 of the embodiment includes a local maximum value detection part 1, a feature peak value selection part 2, and a local maximum value rejection part 3 as shown in FIG. 1. The signal feature extraction apparatus 10 performs processing of steps shown in FIG. 2 and thereby implements a signal feature extraction method of the embodiment.

The signal feature extraction apparatus 10 is a special apparatus formed, for example, by causing a known or dedicated computer including a central processing unit (CPU), a main storage device (RAM: Random Access Memory), and the like to read in a special program. The signal feature extraction apparatus 10 performs the processing, for example, under control of the central processing unit. Data input into the signal feature extraction apparatus 10 or data obtained by the processing is stored, for example, in the main storage device, and the data stored in the main storage device is read out on demand, and used for other processing. At least part of processing parts of the signal feature extraction apparatus 10 may be configured by hardware such as an integrated circuit.

Figure 2:
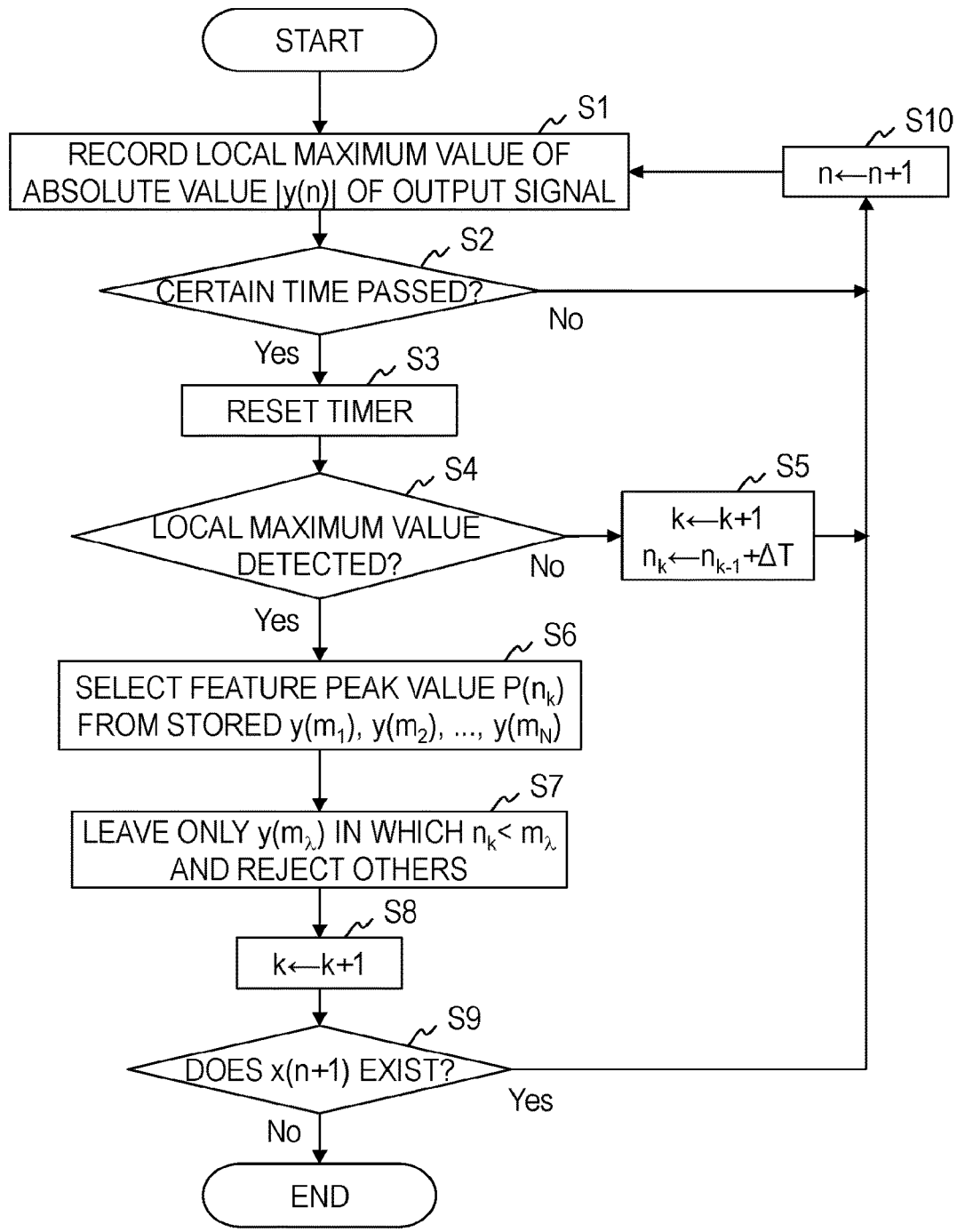
FIG. 2 is a diagram exemplifying a processing procedure of a signal feature extraction method.

Processing procedure of the signal feature extraction method of the embodiment will be described with reference to FIG. 2.

In step S1, the local maximum value detection part 1 receives an output signal y(n) when an input signal x(n) to be analyzed is input into a feature extraction filter, and stores a value of the output signal y(n) together with the time index $m_\lambda$, when an absolute value |y(n)| of the output signal y(n) is equal to or more than a predetermined threshold value and takes a local maximum value, in which a time index at that time is denoted by $m_\lambda$=n.

In step S2, the local maximum value detection part 1 determines whether a timer that measures a time when the local maximum value detection processing is being performed indicates that a certain time has passed. If the certain time has not passed, in step S10, 1 is added to the time index n, and the processing of step S1 is executed again. If the certain time has passed, the timer is reset in step S3, and the processing proceeds to step S4.

In step S4, the local maximum value detection part 1 determines whether the local maximum value detected in step S1 exists. If the local maximum value is not detected, the local maximum value detection part 1 updates a time index $n_k$ and a serial number k of the most recently selected feature peak value $P(n_{k-1})$ to k←k+1, $n_k$←$n_{k-1}$+ΔT in step S5. If the local maximum value is detected, the local maximum value detection part 1 transmits local maximum values y($m_1$), y($m_2$), . . . , y($m_N$) to the feature peak value selection part 2, and the processing proceeds to step S6.

In step S6, the feature peak value selection part 2 receives the stored local maximum values y($m_1$), y($m_2$), . . . , y($m_N$) of the output signal from the local maximum value detection part 1, and selects a feature peak value $P(n_k)$ on the basis of differences from the average time interval ΔT, average logarithmic amplitude log_A, and average phase Φ of past feature peak values. Specifically, the feature peak value $P(n_k)$ is calculated by the above-described formulas (1) and (2). The feature peak value $P(n_k)$ and its time index $n_k$ are transmitted to the local maximum value rejection part 3.

In step S7, the local maximum value rejection part 3 leaves the local maximum value y($m_\lambda$) corresponding to a time index which is $n_k$<$m_\lambda$ among the stored local maximum values y($m_1$), y($m_2$), . . . , y($m_N$) of the output signal and rejects the rest. Then, in step S8, the serial number k is updated to k←k+1.

In step S9, it is determined whether an input signal x(n+1) of a next time n+1 exists. If it exists, 1 is added to the time index n in step 10, and the processing of steps S1 to S9 is executed again. If it does not exist, the processing is terminated.

By configuring as described above, according to the signal feature extraction technique of the invention, a feature peak value is simultaneously and comprehensively evaluated for a plurality of candidates for the feature peak value regarding adequacy of the time interval and the magnitude of amplitude value with relative to the feature peak values detected in the past and adequacy of the phase angle (the phase angle is different if the waveform pattern is different even if equivalent frequency components are included), and it is possible to detect the feature peak value more accurately.

Points of the invention are summarized as follows. When observing an output signal obtained when a signal in which a similar waveform pattern (feature) is continuously repeated is input into an analysis system including at least one or more feature extraction filters (also including, for example, band-pass filters, wavelets, or other filters with nonlinear nature), an output signal of a feature extraction filter highly correlated with the waveform pattern takes a peak value in synchronization with an appearance of features of a target waveform pattern. However, there may be a case where peak values other than a desired peak value such as noise or leakage of other waveform patterns are observed from the output signal of the same feature extraction filter. The invention is one method for selecting a desired peak value (feature peak value) that is desired to be originally acquired from peak values observed in an output signal of a certain feature extraction filter. As the feature peak value desired to be originally acquired, the most likely feature peak value is selected from a plurality of candidate peak values by comprehensively determining whether the following three hypotheses are satisfied: regularity in the time interval with past feature peak values (appearing at approximately constant intervals); consistency of the magnitude of the amplitude value (the magnitude of peak values is approximately equal); and consistency of the phase angle (not only frequency characteristics but also patterns as time waveforms are similar). That is, the invention selects as the desired peak value a feature peak value that is the smallest in difference between a time interval between an observed peak value and an immediately before feature peak value and an average time interval at which a feature peak value can occur, difference between the amplitude of the observed peak value and the average amplitude that the feature peak value can take, and difference between the phase of the observed peak value and the average phase that the feature peak value can take. Furthermore, in order to evaluate the differences, the formula (4) can be used, which corresponds to, by taking logarithm of the stored complex output signal, obtaining features of a complex number having logarithmic amplitude in the real part and phase information in the imaginary part, and evaluating differences in amplitude and phase uniformly as a whole. As a result, even when the behavior of time fluctuation of each value of the average logarithmic amplitude and the average phase as a comparison target of the differences is different, the fluctuation of the values of the differences is averaged, contributing to selection of a stable peak value.

Input signals to be analyzed in the invention are biological signals (for example, an electrocardiogram (ECG, EKG), a pulse wave measured by photoplethysmogram (PPG) or the like, and a respiration curve) related to a physiological phenomenon having arbitrary periodicity including an acoustic signal or heartbeat, pulse, and breathing. The input signals to be analyzed repeat a local waveform pattern having substantially the same size and shape at almost periodic intervals. An output signal of a filter having a high correlation with such a characteristic waveform pattern takes a peak value selectable according to the present invention in synchronization with the appearance of the waveform pattern. In the invention, a measurement method of a biological signal is not questioned. Taking the heartbeat as an example, an object may be an electrocardiogram which is a method for measuring an electric activity associated with the heartbeat or it may be a seismocardiography (SCG) or ballistocardiography (BCG) which measures vibration of skin caused by the heartbeat with an accelerometer. Biological signals not described above may also be included in the analysis objects as long as they have the above characteristics.

Although the embodiment of the present invention has been described above, specific configurations are not limited to the embodiment, and even if design changes and the like are appropriately made without departing from the spirit of the invention, it goes without saying that they are included in the invention. The various processes described in the embodiment may be executed not only in chronological order in accordance with the described order but also in parallel or individually in accordance with processing capability or necessity of an apparatus that executes the processes.

[Program and Recording Medium]

When various processing functions of each apparatus described in the above embodiment are implemented by a computer, processing contents of the functions that each apparatus should have are described by a program. By executing the program by the computer, the various processing functions of each apparatus are implemented on the computer.

The program describing the processing contents can be recorded on a computer-readable recording medium. The computer-readable recording medium may be any medium, for example, a magnetic recording device, an optical disc, a magneto-optical recording medium, and a semiconductor memory.

Distribution of this program is carried out, for example, by selling, transferring, and renting a portable recording medium such as a DVD, CD-ROM, or a flash drive in which the program is recorded. Otherwise, the program can be pre-installed in arbitrary recording medium through the manufacturing process in a factory. Furthermore, the program may be stored in a storage device of a sever computer, and the program may be distributed by transferring the program from the server computer to another computer via a network.

A computer that executes such a program, for example, stores the program recorded in the portable recording medium or the program transferred from the server computer in its own storage device. When processing is executed, the computer reads the program stored in its own recording medium and executes the processing according to the read program. Furthermore, as another mode of execution of the program, the computer may read the program directory from the portable recording medium and execute the processing according to the program, or may sequentially execute, each time a program is transferred from the server computer to the computer, processing according to the received program. In addition, the above-described processing may be executed, not by transferring the program from the server computer to the computer, but by a configuration in which the above-described processing is executed by a so-called ASP (Application Service Provider) type service that achieves a processing function only by giving execution instructions and obtaining results. The program in this form includes information that is used for processing by an electronic computer and conforms to a program (data or the like that is not a direct instruction to a computer but has a characteristic defining processing of the computer).

In this form, the apparatus is configured by executing a predetermined program on a computer, but at least part of the processing contents may be implemented by hardware.

What is claimed is:

1. A signal feature extraction apparatus for extracting a feature peak value of a waveform pattern from an output signal of a feature extraction filter that extracts a waveform pattern of an input signal,
   wherein the feature extraction filter is a linear or nonlinear filter that outputs as the output signal a complex signal having a real part and an imaginary part mutually convertible or approximately convertible by Hilbert transform,
   the signal feature extraction apparatus comprising:
   a local maximum value detection part that stores a time index and a value of the output signal when an absolute value of the output signal is equal to or more than a predetermined threshold value and takes a local maximum value;
   a feature peak value selection part that selects the feature peak value on the basis of a difference between a time interval between the stored time index and a time index of a feature peak value selected immediately before and an average time interval at which the feature peak value can occur, and a difference between a logarithmic amplitude and phase of the output signal corresponding to the stored time index and an average logarithmic amplitude and average phase that the feature peak value can take; and
   a local maximum value rejection part that rejects the stored value of the output signal except the value of the output signal selected as the feature peak value.

2. The signal feature extraction apparatus according to claim 1, wherein
   the feature peak value selection part selects an absolute value of the output signal corresponding to a time index calculated by a following formula as the feature peak value:

$$\operatorname*{argmin}_{m_\lambda}\left[w_1\frac{|m_\lambda - n_0 - \Delta T|^2}{\Delta T^2} + \frac{w_2|\log(|y(m_\lambda)|) - \log\_A|^2 + w_3|\mathrm{angle}(y(m_\lambda)/e^{j\Phi})|^2}{w_4\log\_A^2 + w_5\Phi^2}\right]$$

where, N denotes a number of the stored time indexes, $m_1, \ldots, m_N$ denote the stored time indexes, $y(m_1), \ldots, y(m_N)$ denote the output signals corresponding to the time indexes $m_1, \ldots, m_N$, $\lambda$ denotes each integer of 1 to N, $\Delta T$ denotes the average time interval, $\log\_A$ denotes the average logarithmic amplitude, $\Phi$ denotes the average phase, $w_1, w_2, w_3, w_4$, and $w_5$ denote predetermined weighting factors, angle (•) denotes a phase angle of a complex number •, and $n_0$ denotes an initial value of the time index.

3. The signal feature extraction apparatus according to claim 1, wherein
   the input signal is an electrocardiogram, and
   the feature peak value corresponds to the waveform pattern indicating a heartbeat.

4. A signal feature extraction apparatus for extracting a feature peak value of a waveform pattern from an output signal of a feature extraction filter that extracts a waveform pattern of an input signal,
   wherein the feature extraction filter is a linear or nonlinear filter that outputs as the output signal a complex signal having a real part and an imaginary part mutually convertible or approximately convertible by Hilbert transform,
   the signal feature extraction apparatus comprising:
   a local maximum value detection part that stores a time index and a value of the output signal when an absolute value of the output signal is equal to or more than a predetermined threshold value and takes a local maximum value;
   a feature peak value selection part that selects the feature peak value on the basis of a difference between a time interval between the stored time index and a time index of a feature peak value selected immediately before and an average time interval at which the feature peak value can occur, a difference between an amplitude of the output signal corresponding to the stored time index and an average amplitude the feature peak value can take, and a difference between a phase of the output signal corresponding to the stored time index and an average phase the feature peak value can take; and a local maximum value rejection part that rejects the stored value of the output signal except the value of the output signal selected as the feature peak value.

5. The signal feature extraction apparatus according to claim 4, wherein the input signal is an electrocardiogram, and the feature peak value corresponds to the waveform pattern indicating a heartbeat.

6. A non-transitory computer-readable recording medium on which a program recorded thereon for causing a computer to function as the signal feature extraction apparatus according to any of claim 1, 2, or 4.

7. A signal feature extraction method for extracting a feature peak value of a waveform pattern from an output signal of a feature extraction filter that extracts a waveform pattern of an input signal, wherein the feature extraction filter is a linear or nonlinear filter that outputs as the output signal a complex signal having a real part and an imaginary part mutually convertible or approximately convertible by Hilbert transform, the signal feature extraction method comprising:

a local maximum value detection step in which a local maximum value detection part stores a time index and a value of the output signal when an absolute value of the output signal is equal to or more than a predetermined threshold value and takes a local maximum value;

a feature peak value selection step in which a feature peak value selection part selects the feature peak value on the basis of a difference between a time interval between the stored time index and a time index of a feature peak value selected immediately before and an average time interval at which the feature peak value can occur, and a difference between a logarithmic amplitude and phase of the output signal corresponding to the stored time index and an average logarithmic amplitude and average phase that the feature peak value can take; and a local maximum value rejection step in which a local maximum value rejection part rejects the stored value of the output signal except the value of the output signal selected as the feature peak value.

8. The signal feature extraction method according to claim 7, wherein the feature peak value selection step selects an absolute value of the output signal corresponding to a time index calculated by a following formula as the feature peak value:

$$\operatorname*{argmin}_{m_\lambda}\left[w_1 \frac{|m_\lambda - n_0 - \Delta T|^2}{\Delta T^2} + \right.$$

-continued $$\left. \frac{w_2|\log(|y(m_\lambda)|) - \log\_A|^2 + w_3|\mathrm{angle}(y(m_\lambda)/e^{j\Phi})|^2}{w_4 \log\_A^2 + w_5 \Phi^2}\right]$$

where, N denotes a number of the stored time indexes, $m_1, \ldots, m_N$ denote the stored time indexes, $y(m_1), \ldots, y(m_N)$ denote the output signals corresponding to the time indexes $m_1, \ldots, m_N$, $\lambda$ denotes each integer of 1 to N, $\Delta T$ denotes the average time interval, log_A denotes the average logarithmic amplitude, $\Phi$ denotes the average phase, $w_1, w_2, w_3, w_4$, and $w_5$ denote predetermined weighting factors, angle (•) denotes a phase angle of a complex number •, and $n_0$ denotes an initial value of the time index.

9. The signal feature extraction method according to claim 7, wherein the input signal is an electrocardiogram, and the feature peak value corresponds to the waveform pattern indicating a heartbeat.

10. A signal feature extraction method for extracting a feature peak value of a waveform pattern from an output signal of a feature extraction filter that extracts a waveform pattern of an input signal, wherein the feature extraction filter is a linear or nonlinear filter that outputs as the output signal a complex signal having a real part and an imaginary part mutually convertible or approximately convertible by Hilbert transform, the signal feature extraction method comprising:

a local maximum value detection step in which a local maximum value detection part stores a time index and a value of the output signal when an absolute value of the output signal is equal to or more than a predetermined threshold value and takes a local maximum value;

a feature peak value selection step in which a feature peak value selection part selects the feature peak value on the basis of a difference between a time interval between the stored time index and a time index of a feature peak value selected immediately before and an average time interval at which the feature peak value can occur, a difference between an amplitude of the output signal corresponding to the stored time index and an average amplitude the feature peak value can take, and a difference between a phase of the output signal corresponding to the stored time index and an average phase the feature peak value can take; and a local maximum value rejection step in which a local maximum value rejection part rejects the stored value of the output signal except the value of the output signal selected as the feature peak value.

11. The signal feature extraction method according to claim 10, wherein the input signal is an electrocardiogram, and the feature peak value corresponds to the waveform pattern indicating a heartbeat.

* * * * *